(12) United States Patent
Pellegrini et al.

(10) Patent No.: US 7,584,754 B1
(45) Date of Patent: Sep. 8, 2009

(54) DISPOSABLE EYE PATCH AND METHOD OF MANUFACTURING A DISPOSABLE EYE PATCH

(75) Inventors: Richard L. Pellegrini, Lincoln, RI (US); Steven B. Krupnick, Philadelphia, PA (US)

(73) Assignee: Sperian Eye & Face Protection, Inc., Smithfield, RI (US)

( * ) Notice: Subject to any disclaimer, the term of this patent is extended or adjusted under 35 U.S.C. 154(b) by 555 days.

(21) Appl. No.: 09/988,335

(22) Filed: Nov. 19, 2001

(51) Int. Cl.
*A61F 9/00* (2006.01)

(52) U.S. Cl. .......................................... 128/858; 2/15

(58) Field of Classification Search ............... 602/72, 602/74; 2/11, 15, 2, 439, 440; 128/857–858, 128/846, 853
See application file for complete search history.

(56) References Cited

U.S. PATENT DOCUMENTS

| | | | |
|---|---|---|---|
| 1,161,321 A | 11/1915 | Lush | |
| 1,275,127 A | 8/1918 | Campbell | |
| 1,528,282 A | 3/1925 | White | |
| 2,165,668 A | 7/1939 | Vaccaro | |
| 2,283,752 A * | 5/1942 | Gonsett | 2/15 |
| 2,527,947 A * | 10/1950 | Loos | 604/294 |
| 2,572,638 A | 10/1951 | Loos | |
| 2,643,382 A | 6/1953 | McLeod | |
| 3,068,863 A | 12/1962 | Bowman | |
| 3,092,103 A | 6/1963 | Mower | |
| 3,121,021 A | 2/1964 | Copeland | |
| 3,339,206 A | 9/1967 | Daley | |
| 3,521,630 A | 7/1970 | Westberg et al. | |
| 3,814,095 A | 6/1974 | Lubens | |
| 3,908,645 A | 9/1975 | Sandvig | |
| 4,022,203 A | 5/1977 | Ackley | |
| 4,117,842 A | 10/1978 | Hutchins | |
| 4,122,847 A | 10/1978 | Craig | |
| 4,134,401 A | 1/1979 | Galician | |
| 4,162,542 A | 7/1979 | Frank | |
| 4,331,136 A | 5/1982 | Russell et al. | |
| 4,339,035 A | 7/1982 | Marcus et al. | |
| 4,473,370 A | 9/1984 | Weiss | |
| 4,570,626 A | 2/1986 | Norris et al. | |
| 4,581,877 A | 4/1986 | Wilber | |
| 4,635,625 A | 1/1987 | Teeple | |
| 4,682,371 A | 7/1987 | Heltman | |

(Continued)

FOREIGN PATENT DOCUMENTS

DE 24 29 989 6/1974

(Continued)

OTHER PUBLICATIONS

Absorbing, vol. 2, Issue 2, Oct. 94.

(Continued)

*Primary Examiner*—Michael A. Brown
(74) *Attorney, Agent, or Firm*—Oliff & Berridge, PLC

(57) ABSTRACT

A disposable, laser-resistant eye patch includes at least one sheet member and a metallic layer attached to the sheet member. The eye patch may include two sheet members, with the metallic layer interposed between the sheet members. The eye patch preferably has adhesive applied on a peripheral portion of the eye patch for attaching the eye patch to a wearer's face. The eye patch is preferably sized to fit entirely within the eye socket of a human eye.

54 Claims, 5 Drawing Sheets

U.S. PATENT DOCUMENTS

| | | | |
|---|---|---|---|
| 4,701,962 A | | 10/1987 | Simon |
| 4,709,695 A | * | 12/1987 | Kohn et al. ................. 128/858 |
| 4,719,909 A | | 1/1988 | Micchia et al. |
| 4,790,031 A | * | 12/1988 | Duerer ........................... 2/439 |
| 4,793,002 A | | 12/1988 | Simon |
| 4,793,003 A | | 12/1988 | Riedel et al. |
| 4,862,902 A | | 9/1989 | Goffman |
| 4,867,146 A | * | 9/1989 | Krupnick et al. ............ 128/858 |
| 4,901,738 A | * | 2/1990 | Brink et al. ................. 128/849 |
| 4,944,040 A | | 7/1990 | Riedel et al. |
| 4,951,658 A | | 8/1990 | Morgan et al. |
| 4,969,472 A | * | 11/1990 | Langley et al. .............. 128/858 |
| 4,995,114 A | | 2/1991 | Price, Jr. |
| 5,004,333 A | | 4/1991 | Bruhl, Jr. |
| 5,180,360 A | | 1/1993 | Rhame, Jr. |
| 5,190,810 A | * | 3/1993 | Kirschbaum et al. ........ 442/234 |
| 5,191,897 A | | 3/1993 | Meshel |
| 5,209,718 A | | 5/1993 | McDaniel |
| 5,309,925 A | * | 5/1994 | Policastro ................... 128/849 |
| 5,469,864 A | | 11/1995 | Rosenblatt |
| 5,487,394 A | | 1/1996 | Shiu et al. |
| 5,524,642 A | * | 6/1996 | Rosenblatt ................. 128/849 |
| 5,740,550 A | | 4/1998 | Yavitz |
| 5,769,806 A | | 6/1998 | Radow |
| 5,782,672 A | | 7/1998 | Woodley |
| 5,887,590 A | | 3/1999 | Price |
| 5,918,600 A | * | 7/1999 | Durette ....................... 128/857 |
| 5,970,515 A | | 10/1999 | Fishbaugh |
| 5,980,497 A | | 11/1999 | Yavitz |
| D421,124 S | | 2/2000 | Yavitz |
| D425,623 S | | 5/2000 | Funk |
| 6,090,060 A | | 7/2000 | Radow |
| 6,098,628 A | | 8/2000 | Funk |
| 6,131,208 A | | 10/2000 | Banks |
| 6,149,615 A | | 11/2000 | Gallamore |
| D444,561 S | | 7/2001 | Stein |
| D446,307 S | | 8/2001 | Bassett |
| 6,320,094 B1 | * | 11/2001 | Arnold et al. ................. 602/54 |
| 2004/0212894 A1 | * | 10/2004 | Wilson et al. ............... 359/630 |

FOREIGN PATENT DOCUMENTS

WO      WO 93/06678      4/1993

OTHER PUBLICATIONS

GPT Glendale, Inc., Patient Care Derm-Aid™ Disposables.
GPT Glendale, Inc. Non-Laser Disposable Derm Aid™ Eye Shield.
GPT Glendale, Inc., Patient Care DennAid™ Disposables, Oct. 1999.
GPT Glendale, Inc. Non-Laser Disposable Derm Aid™ Eye Shield, Oct. 1999.
U.S. Appl. No. 10/716,246, filed Nov. 19, 2003 (Arnold et al.).

* cited by examiner

DISPOSABLE EYE PATCH AND METHOD OF MANUFACTURING A DISPOSABLE EYE PATCH

The entire disclosure of application Ser. No. 09/663,382, filed Sep. 15, 2000, now U.S. Pat. No. 6,320,094, is hereby incorporated by reference herein in its entirety.

BACKGROUND OF THE INVENTION

1. Field of Invention

This invention relates to a disposable eye patch. In particular, this invention relates to a disposable eye patch used during surgical and/or professional facial care procedures.

2. Description of Related Art

Cosmetic surgical procedures (e.g., plastic surgery) and professional facial care procedures are becoming increasingly popular. In come cases, patients request such procedures for facial parts such as the nose bridge, forehead, temples, and areas immediately surrounding the eyes. During surgical or other procedures to such facial parts, since the procedures often require very delicate and detailed work, doctors and other professionals must have access to as much unobstructed area as possible. At the same time, the doctors or other professionals need to avoid damaging the patient's eyes by various surgical, medical and cosmetic items, such as abrasion systems, chemicals, air jets, air streams, liquids, medicines, medicine applicators, surgical tools (e.g., scalpels, hemostats, needles, etc.) and other devices.

Therefore, the patient's eyes are often covered by materials such as a surgical tape and gauze while a surgical or facial care procedure is being performed. However, there is a need for more complete access to areas around the patient's eyes and for more reliable protection methods and devices.

U.S. Pat. No. 4,682,371 to Heltman discloses a protective eye patch. This eye patch has several adhesive tabs for securing the eye patch on the patient's eye. However, since the tabs do not entirely adhere the edge of the eye patch, there is a possibility that liquids or medicines may enter a patient's eye covered by this eye patch.

U.S. Pat. No. 3,068,863 to Bowman discloses another type of protective eye patch. This eye patch is designed to keep the eye closed. However, since this patch is adhered onto the patient's eyelid and surrounding eye tissues, this eye patch is not comfortable to wear.

U.S. Pat. No. 3,092,103 to Mower provides an eye patch that has a cushion material on an edge of the eye patch, and allows a patient's eye to move and/or open underneath the eye patch. Because of its large size, this patch is not suitable for many surgical and facial care procedures.

U.S. Pat. No. 4,867,146 to Krupnick et al. discloses an eye patch for preventing opening of an eye and preventing corneal abrasion. This eye patch has adhesive areas around the patch and part of a center part of the eye patch. However, because of the adhesive areas in the center part, it is uncomfortable for the patient to wear the eye patch for a long time. In fact, it is designed for use on an anesthetized patient.

U.S. Pat. No. 5,180,360 to Rhame, Jr. discloses an oval shaped eye patch with a thick inner foam patch or adjustable bladder for adjusting pressure against an eyelid. This patch is quite large, being designed to attach to the outside of the eye socket, and covers some areas of the face that may need to be accessed for some surgical or facial care procedures.

SUMMARY OF THE INVENTION

This invention provides a small size disposable eye patch that allows doctors or other professionals full access to areas around the eyes for surgery and facial care procedures, including laser surgery and laser procedures, and is comfortable for the patient to wear.

A disposable, laser resistant eye patch according to the invention includes at least one sheet member and a metallic layer attached to the sheet member. The eye patch may include two sheet members, with the metallic layer interposed between the sheet members. The eye patch preferably has adhesive applied on a peripheral portion of the eye patch for attaching the eye patch to a wearer's face. The eye patch is preferably sized to fit entirely within the eye socket of a human eye.

These and other features and advantages of this invention are described in or are apparent from the following description of exemplary embodiments.

BRIEF DESCRIPTION OF THE DRAWINGS

An embodiment of the invention will now be described with reference to the accompanying drawings, in which.

DETAILED DESCRIPTION OF PREFERRED EMBODIMENTS

Figure 1:
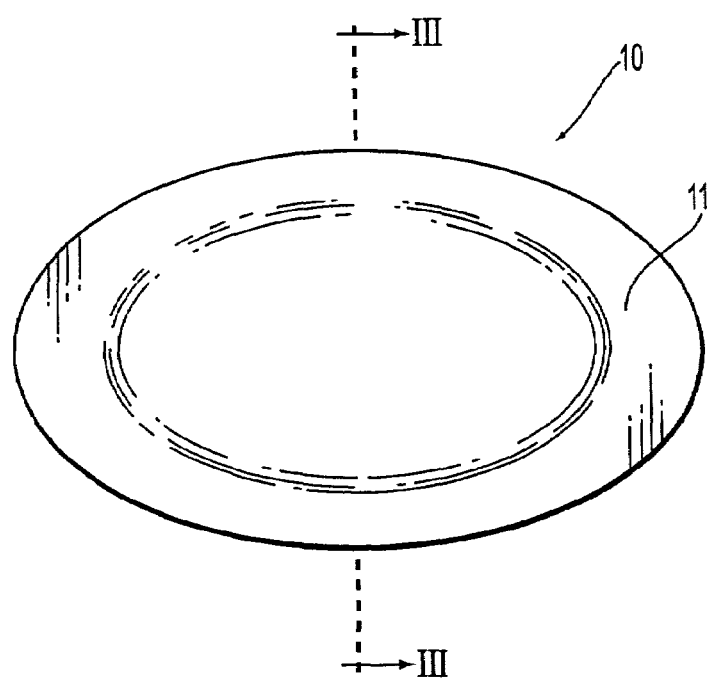
FIG. 1 is a top view of a disposable eye patch according to a first exemplary embodiment of the invention.
Figure 2:
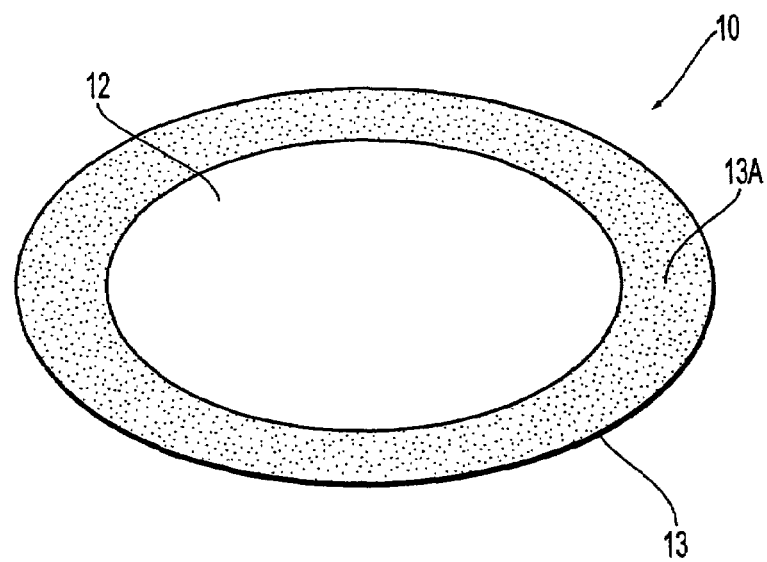
FIG. 2 is a bottom view of the disposable eye patch of FIG. 1.

As shown in FIGS. 1 and 2, a disposable eye patch 10 includes a first sheet member 11 and a second sheet member 12. These first and second sheet members are preferably oval in shape, although other shapes, such as a teardrop shape or the like, are also possible. "Oval" in the context of this application includes elliptical, oblong, and egg shapes. The first sheet member 11 is preferably made of biocompatible foamed plastic material. The second sheet member 12 is also preferably made of biocompatible foamed plastic material.

The eye patch 10 includes a first adhesive layer 13 on one side of the first sheet member 11 for adhering the eye patch 10 onto the tissue surrounding the patient's eye and for adhering the first sheet member 11 to the second sheet member 12. This first adhesive layer 13 may have a plan view size approximately equal to the plan view size of the first sheet member 11 and is preferably made of a pressure-sensitive adhesive (i.e., it may acquire greater adhesion with an adjacent surface as pressure between that surface and the adhesive is increased), preferably a latex-free and hypoallergenic material. The adhesion of the adhesive layer 13 should be strong enough to adhere reliably to the skin but weak enough to be easily removed from the skin after use.

Figure 3:
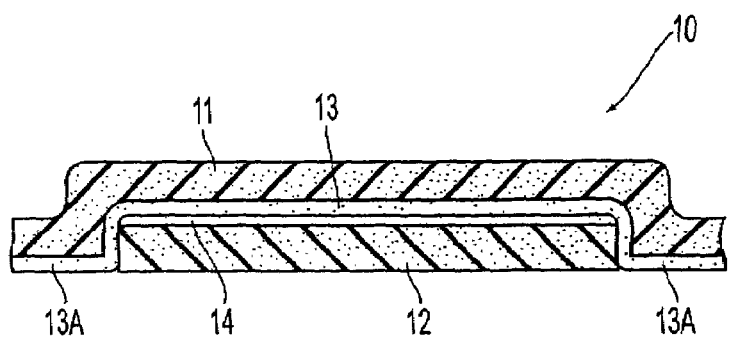
FIG. 3 is a cross-sectional view of the disposable eye patch of FIG. 1.

As shown in FIG. 3, the eye patch 10 may also include a second adhesive layer 14 between the second sheet member 12 and the first adhesive layer 13. The second adhesive layer 14 is not essential, but improves adhesion of the second sheet member 12 to the first sheet member 11. The second adhesive layer 14 may have a plan view size equal to the plan view size of the second sheet member 12. The second adhesive layer 14 may be made of the same material as the first adhesive layer 13.

The first sheet member 11 has a size that sufficiently covers the patient's eye and eyelid when applied. For instance, for an adult patient, the first sheet member 11 preferably has a length of from about 40 mm to about 60 mm, more preferably about 50 mm, and a width of from about 20 mm to about 35 mm, more preferably about 28 mm. The second sheet member 12 preferably joins the first sheet member 11 at a central portion of the first adhesive layer 13 as shown in FIG. 2.

Having the above-described length and width allows the eye patch 10 to fit within the eye socket of a patient, and thus maximizes the facial area accessible to a doctor or other professional. The part of the eye patch 10 that contacts most of the patient's eyelid is free of exposed adhesive. This is more comfortable to the wearer, and allows the eye and eyelid to slightly move underneath the eye patch 10. Specifically, the side of the sheet member 12 facing the eye and eyelid is free of adhesive. This also prevents needless pain or discomfort when the eye patch is removed after use.

A peripheral portion 13A of the first adhesive layer 13, which is not overlapped by the second sheet member 12, should be large enough to provide sufficient adhesion of the eye patch 10 to the area of the face surrounding the eye. For example, the peripheral portion 13A may have a width of approximately 5 mm.

The first sheet member 11 and the second sheet member 12 each preferably have a thickness in a range of from about 0.1 mm to about 5 mm, more preferably from about 0.1 mm to about 2 mm, and even more preferably about 0.5 mm. The appropriate thickness may vary depending upon the type of procedure for which the eye patch is intended to be used, but in general, a thinner eye patch is desired to reduce the bulkiness of the eye patch 10 and increase the comfort of the patient. For example, for a so-called microdermabrasion process, in which aluminum-oxide crystals or the like are discharged from a wand onto a patient's face, an eye patch 10 with a first sheet member 12 with a thickness of about 0.5 mm and a second sheet member 12 with a thickness of about 0.5 mm effectively protects the eyes.

The color of the eye patch 10 may be the natural color of the foamed plastic material, such as off-white, cream, or the like, or any other desired color such as beige, gray, black, fluorescent green, etc.

Figure 4:
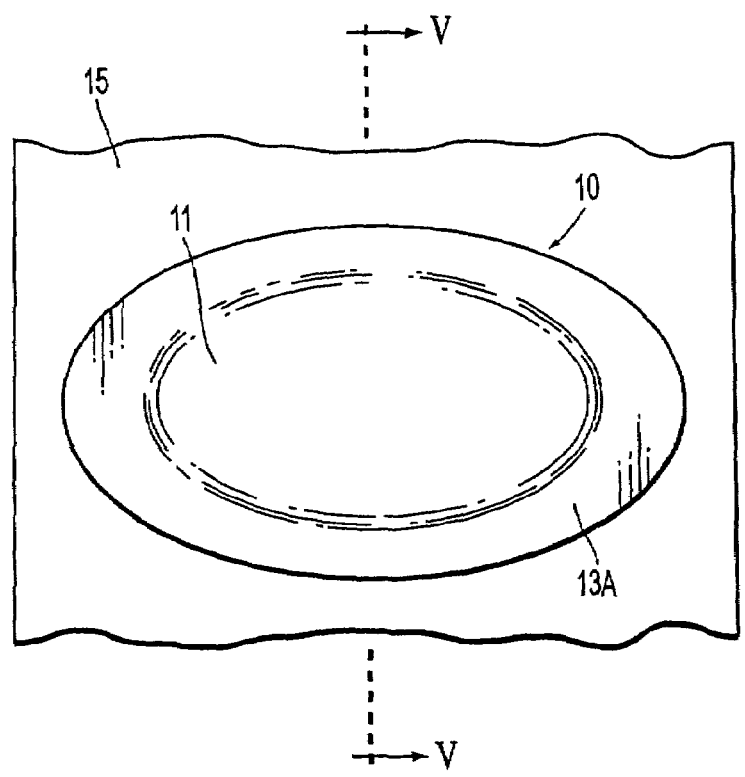
FIG. 4 is a top view of the disposable eye patch of FIG. 1 mounted on a release layer.
Figure 5:
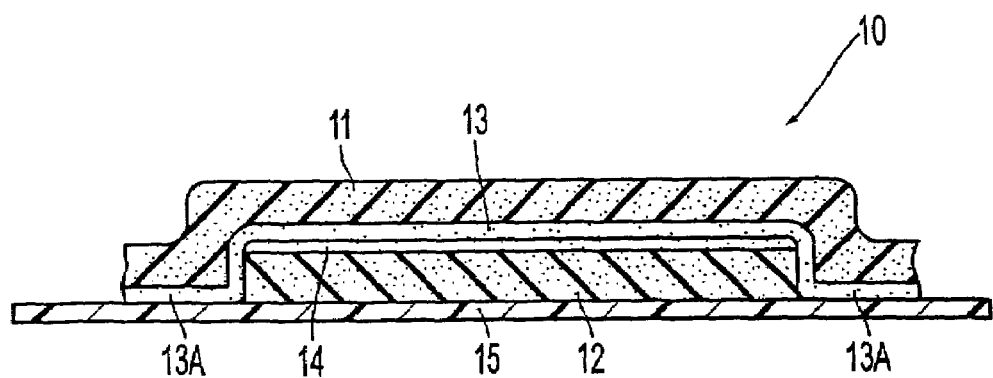
FIG. 5 is a cross-sectional view of the disposable eye patch and the release layer of FIG. 4.

As shown in FIGS. 4 and 5, to prevent the peripheral portion 13A of the adhesive layer 13 and the eye-contacting side of the second sheet member 12 of the eye patch 10 from being contaminated, the peripheral portion 13A of the adhesive layer 13 may be attached to a release layer 15, which is removed prior to use of the eye patch 10. The release layer 15 may, for example, be a waxed paper, plastic film or the like.

Figure 6:
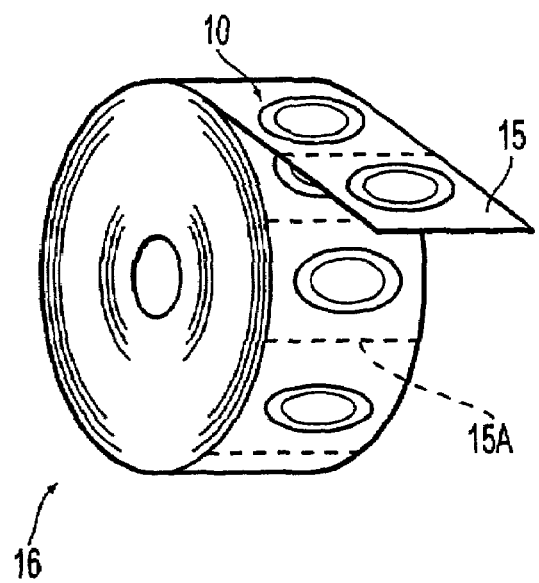
FIG. 6 is a perspective view of the eye patch of FIG. 1 provided on a dispenser roll.

The release layer 15 may be a continuous strip provided in the form of a dispenser roll 16, as shown in FIG. 6, with eye patches 10 provided at a predetermined spacing. This dispenser roll 16 may be provided in a dispenser box (not shown) and fed through a slot or the like provided in the box. The release layer 15 may have serrations 15A in between the eye patches 10 to facilitate separation into discrete units. Providing the release layer 15 and eye patches in the form of the dispenser roll 16 allows convenient dispensing and helps keep the eye patches 10 clean, since the eye patches 10 are not exposed until use.

When the eye patch 10 is to be applied to a patient, the release layer 15 is first peeled off from the disposable eye patch 10. When the release layer 15 has been removed, the peripheral portion 13A of the first adhesive layer 13 is exposed. The eye patch 10 is then positioned over the patient's closed eye and eyelid, and the edge of the eye patch 10 is gently pressed to seal the peripheral portion 13A of the adhesive layer 13 to the facial tissue surrounding the patient's eye and eyelid. After use, the eye patch 10 is gently peeled away from the eye and eyelid.

Figure 7:
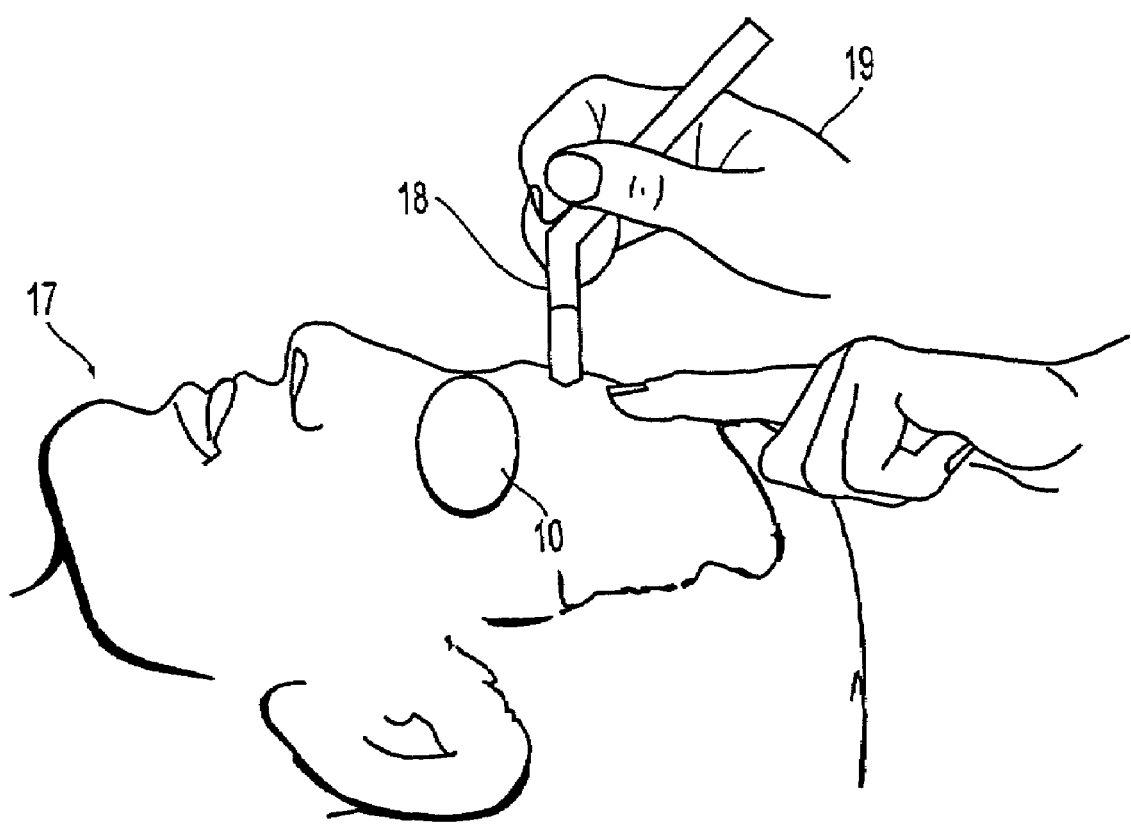
FIG. 7 shows the disposable eye patch of FIG. 1 being used during a facial care procedure.

FIG. 7 shows an example of a patient 17 wearing the disposable eye patch 10 and tissues around the patient's eye. During this treatment, the tissue areas directly around the patient's eye are exposed and accessible to the doctor or therapist 19 using a tool 18, while the eye is protected by the eye patch 10.

A method of manufacturing the eye patch 10 will now be described. First, a sheet material is provided having an adhesive layer coated on one side thereof. The first sheet member 11 and the second sheet member 12 are formed from the sheet material, e.g., by stamping, cutting or the like. Then the first sheet member 11 and the second sheet member 12 are positioned properly with respect to each other and pressed together, with their adhesive-coated surfaces facing each other and coming into contact. Finally, the eye patch 10 is attached to release layer 15, with the exposed peripheral portion 13A of the adhesive on the first sheet member 11 contacting the release layer 15.

This method for manufacturing is not limited to the above-described order of steps. For example, the second sheet member 12 can be cut first, and then adhered to the sheet material. The first sheet member 11 can then be cut in the predetermined shape, thus forming the eye patch 10.

The above-mentioned method of manufacturing an eye patch is relatively fast and easy, since it basically involves only one or two cutting steps and a press-together step, and economical since the only materials needed are a single type of adhesive-coated sheet and a release layer material.

Figure 8:
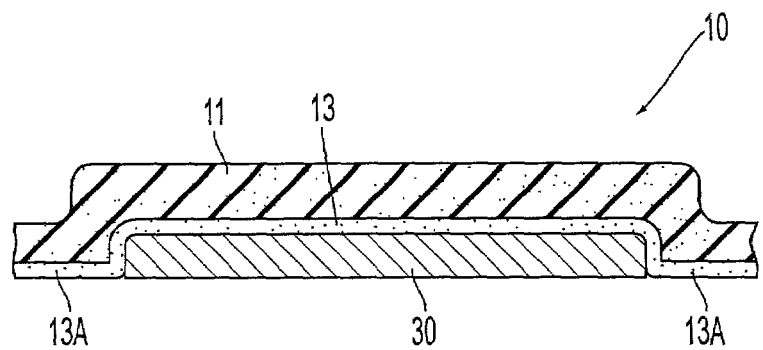
FIG. 8 is a cross-sectional view of a disposable, laser resistant eye patch according to a second exemplary embodiment of the invention.

FIG. 8 is a cross-sectional view of a disposable, laser-resistant eye patch 10 according to a second exemplary embodiment of the invention. As shown in FIG. 8, the eye patch 10 of the second embodiment includes sheet member 11 and metallic layer 30, both of which may have an oval or other shape like that discussed above. The sheet member 11 may be sized as discussed above. One side of the metallic layer 30 may be adhered to the sheet member 11 via adhesive layer 13. The metallic layer 30 may be smaller than the first sheet member 11, and may be positioned such that a peripheral portion 13A of the adhesive layer is exposed. As in the first embodiment, a release layer 15 may be attached to the exposed portion of the adhesive layer 13.

In embodiments, the adhesive layer 13 need not be provided over the entire sheet member 11. For example, in FIG. 8, if the metallic layer 30 is attached by another method such as stitching, thermal bonding, or any other known or later developed attachment method, then it is acceptable to apply the adhesive only to the exposed peripheral portion of the sheet member 11. Furthermore, it should be appreciated that, when the metallic layer 30 is attached to the sheet member 11 by adhesive, the adhesive used to attach the metallic layer to the sheet member 11 may be different from the adhesive provided on the peripheral portion of the sheet member 11 for attaching the eye patch 10 a wearer's face. For example, the adhesive that contacts the wearer's face may be a hypoallergenic and/or pressure-sensitive and/or latex free adhesive as described above, while the adhesive between the metallic layer 30 and the sheet member 11 is an adhesive especially designed to promote good adhesion between the sheet member material, e.g., foamed plastic material, and the metal of the metallic layer.

The metallic layer 30 is laser-resistant, and preferably includes aluminum, either in a pure or alloy form. Other suitable metals include copper, brass, stainless steel, tin and carbon steel, which may also be in either a pure or alloy form. The metallic layer preferably has a thickness greater than 0.001 mm. The thickness may be in a range of from about 0.001 mm to about 1 mm, such as, for example, about 0.04 mm (about 1.5 mils).

The metallic layer 30 may be a metallized polymer film, but preferably is a foil rather than a metallized polymer metal film.

Figure 9:
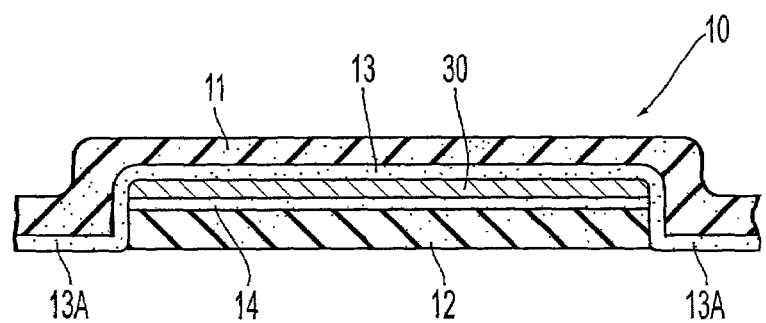
FIG. 9 is a cross-sectional view of a disposable, laser resistant eye patch according to a third exemplary embodiment of the invention.

FIG. 9 is a cross-sectional view of a disposable, laser-resistant eye patch according to a third exemplary embodiment of the invention. The embodiment of FIG. 9 is similar to the embodiment of FIG. 8, except that a second sheet member 12 is provided on the side of the metallic layer 30 opposite the side attached to the first sheet member 11. The second sheet member 12 provides better comfort to the patient by avoiding direct contact between the metallic layer 30 and the patient's face. Thus, the second sheet member 12 preferably has a size equal to or slightly larger than the metallic layer 30. The second sheet member 12 also is preferably smaller than the first sheet member 11 so that the peripheral portion 13A of the adhesive layer 13 remains exposed.

Like the sheet member 11, the sheet member 12 may be attached to the metallic layer 30 by an adhesive layer 14, which may be initially provided on second sheet member 12 or on metallic layer 30. Advantages described above can be achieved by using adhesive coated sheet members 11 and 12 of the same construction or by any other suitable method.

While the invention has been described in conjunction with specific embodiments described above, many equivalent alternatives, modifications and variations will become apparent to those skilled in the art once given this disclosure. Accordingly, the preferred embodiments of the invention as set forth above are considered to be illustrative and not limiting. Various changes to the described embodiments may be made without departing from the spirit and scope of the invention. For example, although the eye patch preferably has a generally oval shape, teardrop shape, or the like, a tab (not shown) may be provided on an edge of the eye patch 10 to allow easy gripping and peeling of the eye patch 10 from the eye and eyelid after use. Such a tab should be large enough for fingers to grip, but otherwise as small as possible to leave as much facial area exposed as possible.

What is claimed is:

1. A disposable, laser-resistant eye patch, comprising:
a sheet member comprising an eye-covering portion sized to fit entirely within a human eye socket in at least one dimension of the eye socket;
a metallic layer attached to the sheet member and protecting an eye from laser light, the metallic layer having a plan-view shape, the plan-view shape including an eyeball-covering area that completely covers an eyeball, the plan-view shape being continuous over the eyeball-covering area, the metallic layer being smaller than the sheet member and not overlapping a peripheral portion of the sheet member; and
an adhesive layer on at least a portion of a periphery of the sheet member.

2. The disposable, laser-resistant eye patch according to claim 1, wherein the sheet member has a thickness in a range of from about 0.1 mm to about 5 mm.

3. The disposable, laser-resistant eye patch according to claim 1, wherein the sheet member has a thickness in a range of from about 0.1 mm to about 2 mm.

4. The disposable, laser-resistant eye patch according to claim 1, wherein the sheet member has a thickness of about 0.5 mm.

5. The disposable, laser-resistant eye patch according to claim 1, wherein the sheet member is made of biocompatible foamed plastic material.

6. The disposable, laser-resistant eye patch according to claim 1, wherein the metallic layer has a thickness greater than 0.001 mm.

7. The disposable, laser-resistant eye patch according to claim 1, wherein the metallic layer has a thickness in a range of from about 0.001 mm to about 1 mm.

8. The disposable, laser-resistant eye patch according to claim 1, wherein the metallic layer has a thickness of about 0.04 mm.

9. The disposable, laser-resistant eye patch according to claim 1, wherein the metallic layer comprises aluminum.

10. The disposable, laser-resistant eye patch according to claim 9, wherein the metallic layer comprises pure aluminum.

11. The disposable, laser-resistant eye patch according to claim 9, wherein the metallic layer comprises an aluminum alloy.

12. The disposable, laser-resistant eye patch according to claim 1, wherein the metallic layer comprises one of copper, brass, stainless steel, tin and carbon steel.

13. The disposable, laser-resistant eye patch according to claim 12, wherein the metallic layer comprises a pure metal.

14. The disposable, laser-resistant eye patch according to claim 12, wherein the metallic layer comprises a metal alloy.

15. The disposable, laser-resistant eye patch according to claim 1, wherein the metallic layer is not part of a metallized polymer layer.

16. A method of protecting a patient's eye during treatment of an adjacent portion of the patient's face, comprising adhering a disposable, laser-resistant eye patch according to claim 1 over said eye and entirely within a corresponding eye socket of said patient in at least one dimension of the eye socket.

17. The method of claim 16, wherein the treatment is a light procedure.

18. The method of claim 16, wherein the treatment is laser surgery.

19. The method of claim 16, wherein the treatment is a laser procedure.

20. The disposable, laser-resistant eye patch according to claim 1, wherein the sheet member is sized to fit entirely inside the eye socket in both a lateral dimension of the eye socket and a vertical dimension of the eye socket.

21. The disposable, laser-resistant eye patch according to claim 1, wherein the metallic layer does not overlap any peripheral portion of the sheet member.

22. The disposable, laser-resistant eye patch according to claim 1, further comprising a tab provided at an edge of the sheet member, the tab facilitating gripping of the eye patch.

23. The disposable, laser-resistant eye patch according to claim 1, wherein the plan-view shape is continuous over its entirety.

24. The disposable, laser-resistant eye patch according to claim 1, wherein:
the sheet member is on one side of the metallic layer; and any layer present on the other side of the metallic layer does not overlap the adhesive layer on at least a portion of the periphery of the surface of the sheet member.

25. A disposable, laser-resistant eye patch, comprising:
a sheet member comprising an eye-covering portion sized to fit entirely within a human eye socket in at least one dimension of the eye socket;
a laser-resistant layer of foil or film attached to the sheet member for protecting an eye from laser light, the laser-resistant layer being smaller than the sheet member and not overlapping a peripheral portion of the sheet member; and
an adhesive layer on at least a portion of a periphery of the sheet member.

26. The disposable, laser-resistant eye patch according to claim 25, wherein the laser-resistant layer is a metal foil.

27. The disposable, laser-resistant eye patch according to claim 25, wherein the laser-resistant layer does not overlap any peripheral portion of the sheet member.

28. The disposable, laser-resistant eye patch according to claim 25, wherein the sheet member has a thickness in a range of from about 0.1 mm to about 5 mm.

29. The disposable, laser-resistant eye patch according to claim 25, wherein the sheet member has a thickness in a range of from about 0.1 mm to about 2 mm.

30. The disposable, laser-resistant eye patch according to claim 25, wherein the sheet member has a thickness of about 0.5 mm.

31. The disposable, laser-resistant eye patch according to claim 25, wherein the sheet member is made of biocompatible foamed plastic material.

32. The disposable, laser-resistant eye patch according to claim 25, wherein the sheet member is sized to fit entirely inside the eye socket in both a lateral dimension of the eye socket and a vertical dimension of the eye socket.

33. The disposable, laser-resistant eye patch according to claim 25, further comprising a tab provided at an edge of the sheet member, the tab facilitating gripping of the eye patch.

34. A method of protecting a patient's eye during treatment of an adjacent portion of the patient's face, comprising adhering a disposable, laser-resistant eye patch according to claim 25 over said eye and entirely within a corresponding eye socket of said patient in at least one dimension of the eye socket.

35. The method of claim 34, wherein the treatment is a light procedure.

36. The method of claim 34, wherein the treatment is laser surgery.

37. The method of claim 34, wherein the treatment is a laser procedure.

38. The disposable, laser-resistant eye patch according to claim 25, wherein the laser-resistant layer has a plan-view shape, the plan-view shape including an eyeball-covering area that completely covers an eyeball, the plan-view shape being continuous over the eyeball-covering area.

39. The disposable, laser-resistant eye patch according to claim 25, wherein:
the sheet member is on one side of the laser-resistant layer; and
any layer present on the other side of the laser-resistant layer does not overlap the adhesive layer on at least a portion of the periphery of the surface of the sheet member.

40. A disposable, laser-resistant eye patch, comprising:
a sheet member comprising an eye-covering portion sized to fit entirely within a human eye socket in at least one dimension of the eye socket;
a metallic layer that protects an eye from laser light, the sheet member being on only one side of the metallic layer, the metallic layer being smaller than the sheet member and not overlapping a peripheral portion of the sheet member; and
an adhesive layer on at least a portion of a periphery of the sheet member.

41. The disposable, laser-resistant eye patch according to claim 40, wherein the metallic layer is a metal foil.

42. The disposable, laser-resistant eye patch according to claim 40, wherein the metallic layer does not overlap any peripheral portion of the sheet member.

43. The disposable, laser-resistant eye patch according to claim 40, wherein the sheet member has a thickness in a range of from about 0.1 mm to about 5 mm.

44. The disposable, laser-resistant eye patch according to claim 40, wherein the sheet member has a thickness in a range of from about 0.1 mm to about 2 mm.

45. The disposable, laser-resistant eye patch according to claim 40, wherein the sheet member has a thickness of about 0.5 mm.

46. The disposable, laser-resistant eye patch according to claim 40, wherein the sheet member is made of biocompatible foamed plastic material.

47. The disposable, laser-resistant eye patch according to claim 40, wherein the sheet member is sized to fit entirely inside the eye socket in both a lateral dimension of the eye socket and a vertical dimension of the eye socket.

48. The disposable, laser-resistant eye patch according to claim 40, further comprising a tab provided at an edge of the sheet member, the tab facilitating gripping of the eye patch.

49. A method of protecting a patient's eye during treatment of an adjacent portion of the patient's face, comprising adhering a disposable, laser-resistant eye patch according to claim 40 over said eye and entirely within a corresponding eye socket of said patient in at least one dimension of the eye socket.

50. The method of claim 49, wherein the treatment is a light procedure.

51. The method of claim 49, wherein the treatment is laser surgery.

52. The method of claim 49, wherein the treatment is a laser procedure.

53. The disposable, laser-resistant eye patch according to claim 40, wherein the metallic layer has a plan-view shape, the plan-view shape including an eyeball-covering area that completely covers an eyeball, the plan-view shape being continuous over the eyeball-covering area.

54. The disposable, laser-resistant eye patch according to claim 40, wherein:
any layer present on the other side of the metallic layer does not overlap the adhesive layer on at least a portion of the periphery of the surface of the sheet member.

* * * * *